US008993558B2

(12) United States Patent
Adams

(10) Patent No.: US 8,993,558 B2
(45) Date of Patent: Mar. 31, 2015

(54) COMPOSITIONS COMPRISING A CALCIUM CHANNEL BLOCKER OR A CALMODULIN BLOCKER FOR USE IN THE REMOVAL OF HYPERPLASTIC SKIN LESIONS

(76) Inventor: Kenneth W. Adams, North York (CA)

( * ) Notice: Subject to any disclaimer, the term of this patent is extended or adjusted under 35 U.S.C. 154(b) by 0 days.

(21) Appl. No.: 13/127,147

(22) PCT Filed: Oct. 29, 2009

(86) PCT No.: PCT/CA2009/001560
§ 371 (c)(1),
(2), (4) Date: Jul. 5, 2011

(87) PCT Pub. No.: WO2010/048722
PCT Pub. Date: May 6, 2010

(65) Prior Publication Data
US 2011/0319382 A1    Dec. 29, 2011

(30) Foreign Application Priority Data
Oct. 31, 2008 (CA) ....................... 2642508

(51) Int. Cl.
*A61K 31/00* (2006.01)
*A61K 31/275* (2006.01)
*A61K 31/44* (2006.01)
*A61K 31/54* (2006.01)
*A61K 31/549* (2006.01)
*A61K 9/00* (2006.01)
*A61K 31/277* (2006.01)
*A61K 31/4422* (2006.01)
*A61K 31/554* (2006.01)
*A61K 45/06* (2006.01)
*A61K 47/10* (2006.01)
*A61K 47/24* (2006.01)

(52) U.S. Cl.
CPC ............ *A61K 31/549* (2013.01); *A61K 9/0014* (2013.01); *A61K 9/0019* (2013.01); *A61K 9/0034* (2013.01); *A61K 31/277* (2013.01); *A61K 31/4422* (2013.01); *A61K 31/554* (2013.01); *A61K 45/06* (2013.01); *A61K 47/10* (2013.01); *A61K 47/24* (2013.01)
USPC .... 514/211.07; 514/523; 514/356; 514/225.8

(58) Field of Classification Search
USPC .......................... 514/211.07, 523, 356, 225.8
See application file for complete search history.

(56) References Cited

U.S. PATENT DOCUMENTS

| | | | |
|---|---|---|---|
| 3,485,847 A | | 12/1969 | Bossert et al. |
| 5,552,162 A | * | 9/1996 | Lee ............... 424/646 |
| 5,925,376 A | * | 7/1999 | Heng .............. 424/451 |
| 6,344,461 B1 | * | 2/2002 | Breton et al. ........ 514/277 |
| 6,734,192 B1 | | 5/2004 | Keller |
| 2004/0253300 A1 | | 12/2004 | Easterling |
| 2005/0020569 A1 | | 1/2005 | Easterling |
| 2006/0216338 A1 | | 9/2006 | Easterling |
| 2008/0139584 A1 | | 6/2008 | Kopacki |

FOREIGN PATENT DOCUMENTS

| | | |
|---|---|---|
| CA | 2427757 A1 | 5/2002 |
| WO | 02085292 A2 | 10/2002 |
| WO | 03034999 A2 | 5/2003 |

OTHER PUBLICATIONS

Oster (Foot Disorders Alternative Health and Herbs Remedies (2005, p. 1-5).*
Sterling et al. British J. of Dermatology (2001); 144; 4-11).*
Notice of Transmittal of International Preliminary Report on Patentability (mailed May 12, 2011), International Preliminary Report on Patentability (issued May 3, 2010), and Written Opinion of Searching Authority (completed Feb. 4, 2010).
International Search Report and Written Opinion (mailed Feb. 11, 2010).
Niczyporuc et al., Preliminary study on the effect of the selected calmodulin antagonists on the skin, Roczniki Akademii Medycznej w Bialymstoku, 1996, vol. 41, pp. 515-524.
Humbert et al., Calmodulin Inhibitor Therapy in Psoriasis, Archives of Dermatology, Aug. 1986, vol. 122, pp. 856-857.
McFadden et al., Topically Applied Verapamil Hydrochloride Inhibits Tuberculin-Induced Delayed-Type Hypersensitivity Reactions in Human Skin, Journal of Investigative Dermatology, 1992, vol. 99, pp. 784-786.
Doong et al., The 1996 Lindberg Award: Calcium Antagonists Alter Cell Shape and Induce Procollagenase Synthesis in Keloid and Normal Human Dermal Fibroblasts, Journal of Burn Care and Rehabilitation, Nov.-Dec. 1996, vol. 17, pp. 497-514.
Boddeke et al., Trends in Pharmacologic Sciences (1989) 10:397.
Triggle et al.. Trends in pharmacologic Sciences (1989) 10:370.
Inoue et al. (1993).
Hunter et al. (1993).
Hori et al. (1993).
Pourtier-Man/anedo et al. (1992).
Boesch & Loor (1994).
Zacherlet al. (1994).
Shirai et al. (1991).
Morris et al. (1991).
Muller et al. (1994).
Miyamoto et al. (1992).
Thalhammer et al. (1994).

(Continued)

*Primary Examiner* — Shirley V Gembeh
(74) *Attorney, Agent, or Firm* — Jeffrey S. Melcher; Manelli Selter PLLC

(57) ABSTRACT

A composition, use of and a method of removing a hyperplastic skin lesion on a mammal comprising administering to the lesion or locus thereof a therapeutically effective amount of a composition comprising a blocker selected from the group consisting of a calcium channel blocker, a metabolite thereof, a calmodulin blocker and a metabolite thereof and a pharmaceutically acceptable diluent or carrier.

6 Claims, No Drawings

(56) References Cited

OTHER PUBLICATIONS

Bear (1994).
Ohi et al. (1992).
Fitch et al., "Topical verapamil HCl, Topical Trifluoperazine, and Topical Magnesium Sulfate for the Treatment of Peyronie's Disease—A Placebo-Controlled Pilot Study", Journal of Sexual Medicine, vol. 4, No. 2, Mar. 2007, pp. 477-484.
Baisch et al., "Hyperplastic scars and keloids; Part II: surgical and non-surgical treatment modalities", HNO Dec. 2006, pp. 981-994.
European Search Report mailed Mar. 26, 2012.

* cited by examiner

COMPOSITIONS COMPRISING A CALCIUM CHANNEL BLOCKER OR A CALMODULIN BLOCKER FOR USE IN THE REMOVAL OF HYPERPLASTIC SKIN LESIONS

CROSS-REFERENCE TO RELATED APPLICATIONS

This application is a national stage entry under 35 U.S.C. 371 of International Application No. PCT/CA2009/001560, filed 29 Oct. 2009, designating the United States. This application claims foreign priority under 35 U.S.C. 119 and 365 to Canadian Patent Application No. 2,642,508, filed 31 Oct. 2008. The complete contents of these applications are incorporated herein by reference.

FIELD OF THE INVENTION

This invention relates to a pharmacological treatment for eliminating hyperplastic lesions of the dermis and epidermis layers of the skin such as calluses, corns, plantar warts, hyperplastic scarring, genital warts, keloids, cutaneous warts, skin tags, and the like, particularly, by topical application of compositions comprising a calcium channel or calmodulin blocker.

BACKGROUND OF THE INVENTION

Hyperplastic skin lesions, such as calluses, corns, plantar warts, hyperplastic scarring, genital warts, cutaneous warts, skin tags, and the like are potentially infectious, particularly, genital warts which are a sexually transmitted disease. For hygienic, as well as cosmetic reasons, these warts and skin tags frequently need to be removed.

Hyperplastic skin lesions can result from multiple causes. With psoriasis, the mechanism causing hyperplastic thickening of the skin to form psoriatic plaques is unknown, but appears to be a cell mediated autoimmune process. Areas of the skin subject to excessive repetitive trauma from thermal, chemical or physical means can cause thickening and hypertrophy of the stratum Corneum layer of the epidermis to produce callouses and corns, which are most common on the hands and feet from ill-fitting shoes, or repetitive activities related to work or leisure. Chronic infections can also induce hyperplastic scaring especially in certain individuals predisposed to keloids and other forms of scars that are associated with excessive collagen formation. Other know causes of hyperplasia of the skin are viral infections of the skin that also cause a hyperplasia of the epidermal layers to form pathological lesions such as plantar warts, genital warts, cutaneous warts, skin tags, and the like are potentially infectious, particularly, genital warts which are a sexually transmitted disease. For hygienic, functional, comfort, as well as cosmetic reasons, a safe and painless method for treating these medical conditions associated with hyperplasia of the skin need to be removed/treated.

Any suitable antagonist, generally, of neuronal voltage-dependent $Ca^{++}$ channels may be used to reduce or prevent AIDS related vision loss, myelopathy, or dementia. Examples are Nifedipine, mioflazine, flunarizine, bepridil, lidoflazine, Ranolazine, Nisoldipine, Nicardipine, PN200-110, Felodipine, Amlodipine. Preferred calcium channel antagonists include, but are not limited to, the following drugs, of which the most preferred are those that are capable of crossing the blood brain barrier, for example, nimodipine (Miles Pharmaceuticals, West Haven, Conn.) Smith Kline drug no. 9512 (Smith Kline, French Beecham, Philadelphia, Pa.), and diproteverine (Smith, Kline, French-Beecham). Less preferred antagonists are those that are less CNS permeable, for example, verapamil (Calan, G.D. Searle & Co., Chicago, Ill.; Isoptin, Knoll, Whippany, N.J.), nitrendipine, diltiazem (Cardizem, Marion, Kansas City, Mo.), and nifedipine, U.S. Pat. No. 3,485,847, hereby incorporated by reference (Procardia, L Pfizer, NY, N.Y.; Adalat, Miles). Other $Ca^{2+}$ channel antagonists which may be useful are mioflazine, flunarizine, bepridil, lidoflazine, CERM-196, R 58735, R-56865, Ranolazine, Nisoldipine, Nicardipine, PN200-110, Felodipine, Amlodipine, R-(−)-202-791, and R-(+) Bay K-8644 (Miles, Bayer), whose chemical formulae are described in Boddeke et al., Trends in Pharmacologic Sciences (1989) 10:397 and Triggle et al., Trends in pharmacologic Sciences (1989) 10:370.

For patients suffering from psoriasis, over 80% will experience hyperplastic thickening of the skin called a psoriatic plaques. Current treatments to control psoriatic plaques involve treatments to suppress the immune response causing the plaques or to us keratolytic agents to soften and remove the plaques. The effectiveness of keratolytic topical agents is that they tend to be irritating not only to the areas of skin affected by the psoriatic process, but also to the healthy surrounding skin which they invariably come in contact with.

Keratolytic agents are also used to treat corns and calluses. Current treatments for corns using keratlytic or skin softening agents also tend to be irritating not only to the areas of skin affected by the psoriatic process, but also to the healthy surrounding skin which they invariably come in contact with. And shaving, abrasive methods also tend to wear through at the thinnest areas of these lesions being treated causing pain and bleeding which prevents there complete removal which helps to ensure there recurrence.

Current treatments for wart removal are surgical excision or repeated application of a toxic chemical to burn and/or dissolve/soften the skin to kill skin cells that are infected. Other methods to kill infected skin tissue involve extreme heating, for example, laser, electro-cautery and the like or extreme cooling such as by liquid nitrogen, or coolant sprays to freeze the lesion and bordering tissues. Unfortunately these methods invariably also destroy healthy skin that is continuous with these viral lesions, resulting in a large area of tissue destruction and a large painful wound that often takes weeks to heal.

Current treatments for wart removal are frequently painful and require prolonged and frequently multiple treatments while having a high rate of recurrence. Wart removal is often ineffective since the pain, discomfort and associated disability often causes patients to terminate their treatment before the virus has been cleared.

Pharmaceutical compositions comprising a calcium channel blocker, particularly verapamil, in combination with a quinoline are known to treat viral infections (U.S. Pat. No. 6,734,192 B1—Keller, Robert H., issued May 11, 2004), particularly HIV. United States Patent Application No. 20040253300, —Easterling, W. Jerry, published Dec. 16, 2004 describes a topical, transdermal medicament for use in treating existing scars comprising: a carrier host agent for facilitating non-invasive, transdermal delivery of a calcium antagonist into scar tissue; a therapeutic dosage of a calcium channel blocker agent suspended in said carrier host agent. The calcium channel blocker is preferably verapamil.

United States Patent Application No. 20050020569, —Easterling. W. Jerry, published Jan. 27, 2005 describes a medicament for use in reducing fibrosis in elastic tissues of the human male comprising: a transdermal carrier compound for facilitating non-invasive, transdermal delivery of calcium channel blocker agents to internal tissues of the human penis; a calcium channel blocker agent dispersed in said carrier means. The calcium channel blocker is preferably verapamil.

United States Patent Application No. 20060216338, —Easterling, W. Jerry, published Sep. 28, 2006 describes a medicament for use in the treatment of tissue disorders involving collagen degeneration, comprising: a carrier compound for facilitation non-invasive, transdermal delivery of calcium channel blocker agents in human recipients; and a calcium channel blocker agent dispersed in said carrier means.

United States Patent Application No. 20080139584, —Kopacki, Matthew H., published Jun. 12, 2008 describes a method for healing a wound, comprising the steps of: topically administering a wound healing composition to a wounded area, wherein the wound healing composition comprises: a first medicament characterized as a calcium channel blocker or pharmaceutically acceptable salts or solvates thereof: a second medicament characterized as a hemorrheologic agent or pharmaceutically acceptable salts or solvates thereof; and a dermal penetrating agent or pharmaceutically acceptable salts or solvates thereof.

Verapamil is a known Ca channel blocker and is a competitive inhibitor of P-glycoprotein, as described by Inoue et al. (1993); Hunter et al. (1993); Hori et al. (1993); Pourtier-Manzanedo et al. (1992); Boesch & Loor (1994); Zacherl et al. (1994); Shirai et al. (1991); Morris et al. (1991); Muller et al. (1994); and Miyamoto et al. (1992). Thalhammer et al. (1994) showed that P-glycoprotein-mediated transport of the cationic dye, acridine orange, across the bile canaliculi was inhibited by cyclosporine A and verapamil.

The ATP-15 dependent transport of amphiphilic cations across the hepatocyte canalicular membrane by p-glycoprotein was also studied by Muller et al. (1994). Transport of permanently charged amphiphilic cations was inhibited by verapamil, quinidine and daunorubicin (an antibiotic). Bear (1994) showed that verapamil, colchicine, vinblastine daunomycin and (50 microM) blocked an outwardly-rectifying chloride channel that was proposed to be associated with p-glycoprotein expression. Obi et al. (1992) used the calcium-channel blocker, verapamil, with adriamycin in chemotherapy for superficial bladder cancer.

Verapamil hydrochloride is benzeneacetonitrile α-[3-[[2-(3,4-dimethoxyphenyl)ethyl]-methylamino]propyl]-3,4-dimethoxy-α-(1-methyl-ethyl) hydrochloride; also termed CALAN™ and ISOPTIN™, and available from Searle, Knoll and Parke-Davis.

However, none of the prior art discloses the use of compositions comprising a calcium channel or a calmodulin blocker by topical application for the elimination of hyperplastic skin lesions of the dermis and epidermis, such as plantar warts, hyperplastic scarring, genital warts, cutaneous warts, skin tags.

Thus, there is still a serious need for a pharmaceutical treatment of aforesaid warts and the like.

SUMMARY OF THE INVENTION

It is an object of the present invention to provide an improved treatment for the removal of hyperplastic lesion of the dermis and epidermis, such as psoriatic lesions and psoriatic plaques, calluses, corns, warts, skin tags and the like.

Accordingly, in one aspect the invention provides a method of removing an hyperplastic skin lesion on a mammal comprising administering to said lesion or locus thereof a therapeutically effective amount of a composition comprising a blocker selected from the group consisting of a calcium channel blocker, a metabolite thereof, a calmodulin blocker and a metabolite thereof and a pharmaceutically acceptable diluent or carrier.

Preferably, the calcium channel blocker is verapamil, diltiazem or felodipine.

Preferably, the calmodulin blocker is trifluoperazine.

Preferably, the hyperplastic skin lesion is selected from the group consisting of plantar warts, cutaneous warts, genital warts and skin tags.

Preferably, also, the hyperplastic skin lesion is selected from the group consisting of psoriatic lesions, psoriatic plaques, calluses, corns, plantar warts, genital warts, cutaneous warts, skin tags and the like.

In a further aspect the invention provides a use of a therapeutically effective amount of a pharmaceutical composition for the removal of an hyperplastic skin lesion on a mammal, said composition comprising a blocker selected from the group consisting of a calcium channel blocker, a metabolite thereof, a calmodulin blocker and a metabolite thereof and a pharmaceutically acceptable diluent or carrier.

Preferably, the invention provides a use as hereinabove defined wherein said calcium channel blocker is verapamil, diltiazem or felodipine.

Preferably, the calmodulin blocker is trifluoperazine.

Preferably, the invention provides a use as hereinabove defined wherein said hyperplastic skin lesion is selected from the group consisting of plantar warts, cutaneous warts, genital warts and skin tags.

Preferably, also, the invention provides a use as hereinabove defined wherein said hyperplastic skin lesion is selected from the group consisting of psoriatic lesions and psoriatic plaques, calluses, corns, plantar warts, genital warts, cutaneous warts, skin tags and the like.

The invention involves the local administration of a therapeutically effective amount of the pharmaceutical composition according to the invention as a locally applied injection, or topically as a cream, gel, ointment, patch or the like.

In preferred embodiments, the invention comprises topical ointments or creams applied to cutaneous lesions which effectively treat viral and some non-viral skin lesions by causing involution and ultimately elimination of these cutaneous pathologies.

Thus, I have found that local administration of a calcium channel blocker, calmodulin blocker or metabolites thereof dissolved in or in admixture with a carrier directly to the skin of viral lesions are therapeutically effective in clearing warts, skin tags, and other hyperplastic lesions of the skin.

In preferred embodiments, the invention comprises the administration of verapamil, diltiazem, trifluoperazine or felodipine dissolved in a solution, topically to the cutaneous lesion at a minimum of once, but preferably several times per day, directly to the lesion.

As used herein, reference to the calcium channel and calmoduline blocker drug also includes all of the pharmaceutically effective forms of the drug, such as the salts, and chelates and the like which may provide sustained release of the therapeutic calcium channel or calmoduline blocker active ingredient.

The preferred verapamil-based gel of the present invention includes two constituent preparations, namely, Lecithin Isopropyl Myristate Reagent and Pluronic F1 27 Gel 20%.

Other calcium channel blockers of use in the practice of the invention include benzothiazepines, e.g. Diltiazem, dihydropyridines, e.g. Amlodipine, Felodipine, Isradipine, Nicardipine, Nimodipine and Nisoldpine, and the fast sodium inward channel inhibitor—Bepridil.

DETAILED DESCRIPTION OF PREFERRED EMBODIMENTS

Preparation of the compositions of use in the practise of the invention may be carried out as follows:

A. 5-[N-(3,4-Dimethoxyphenethyl)-N-methylamino]-2-(3,4dimethoxyphenyl)-2-isopropylvaleronitrile hydrochloride (Verapamil)

1. Add 200 grams of Verapamil HCl powder to 300 grams of liquid Ethoxy Diglycol Reagent.
2. Manually mix the contents of step 1 above while adding 500 grams of Lipoderm PCCA Base™ to produce a total volume of 1,000 mls. While continuing the mixing heat gradually to 70 degrees Celsius and maintain this temperature for 2 hours then allow mixture to cool to room temperature.
3. Then allow mixture to cool to room temperature.
4. Once cooled to room temperature process the 1,000 ml mixture from step 2, through Dermamill (a mechanical three role mill)
5. The resulting mix of Verapamil ointment 200 mg/ml can then be packaged and dispensed in amber syringes of appropriate size and protected from light. Store at room temperature.

B. (+)-cis-3-Acetoxy-5-(2-dimethylaminoethyl)-2,3-dihydro-2-(4-methoxyphenyl)-1,5-benzothiazapin-4(5H)-one hydrochloride; (2S,3S)-5-(2-Dimethylaminoethyl)-2,3,4,5-tetrahydro-2-(4-methyphenyl)-4-oxo-1,5-benzothiazepin-3-yl acetate hydrochloride (Diltiazem)

1. Add 100 grams of Diltiazem HCl powder to 100 grams of liquid Ethoxy Diglycol Reagent.
2. Manually mix the contents of step 1 above while adding 800 grams of Lipoderm PCCA Base™ to produce a total volume of 1,000 mls. While continuing the mixing heat gradually to 70 degrees Celcius and maintain this temperature for 2 hours then remove heat source.
3. Then allow mixture to cool to room temperature.
4. Once cooled to room temperature process the 1,000 ml mixture from step 2, through Dermamill (a mechanical three role mill)
5. The resulting mix of Diltiazem ointment 100 mg/ml can then be packaged and dispensed in amber syringes of appropriate size and protected from light. Store at room temperature.

C. H-154/82. Ethyl methyl 4-(2,3-dichlorophenyl)-1,4-dihydro-2,6-dimethylpyridine-3,5-dicarboxylate (Felodipine)

1. Add 100 grams of Felodipine powder to 300 grams of liquid Ethoxy Diglycol Reagent.
2. Manually mix the contents of step 1 above while adding 600 grams of Lipoderm PCCA Base™ to produce a total volume of 1,000 mls. While continuing the mixing heat gradually to 70 degrees Celcius and maintain this temperature for 2 hours then remove heat.
3. Then allow mixture to cool to room temperature.
4. Once cooled to room temperature process the 1,000 ml mixture from step 2, through Dermamill (a mechanical three role mill)
5. The resulting mix of Felodipine ointment 100 mg/ml can then be packaged and dispensed in amber syringes of appropriate size and protected from light. Store at room temperature.

D. CAS-117-89-5 10-[3-(4-Methylpiperazin-1-yl)propyl]-2-trifluoromethyl-phenothiazine dihydrochloride (Trifluoperazine)

1. Add 30 grams of Trifluoperazine powder to 60 grams of liquid Ethoxy Diglycol Reagent.
2. Manually mix the contents of step 1 above while adding 710 grams of Lipoderm PCCA Base™ to produce a total volume of 1,000 mls. While continuing the mixing heat gradually to 70 degrees Celcius and maintain this temperature for 2 hours then remove from heat source.
3. Then allow mixture to cool to room temperature.
4. Once cooled to room temperature process the 1,000 ml mixture from step 2, through Dermamill (a mechanical three role mill)
5. The resulting mix of Trifluoperazine ointment 30 mg/ml can then be packaged and dispensed in amber syringes of appropriate size and protected from light. Store at room temperature.

EXAMPLE 1

A mixture of verapamil dissolved at a concentration of 200 mg/ml in an ointment was applied in small amounts directly to veneral warts on the penis and scrotum of a 25 year old male 2-3 times daily with clearance within about two weeks.

EXAMPLE 2

A mixture of verapamil dissolved at a concentration of 200 mg/ml in an ointment was applied in small amounts directly to a single large and very painful 9 mm diameter plantar wart on the right foot of a 17 year old male. The patient used the cream for about 4 or 5 days, then forgot to take it again. After about 8-10 days the plantar wart had dramatically shrunk in size to the point that he was walking without discomfort. And after one month it had completely disappeared. The patient had only used the topical verapamil initially for 4-6 days, but when he was reassessed after 3 months there was no evidence of the plantar wart.

EXAMPLE 3

A mixture of verapamil dissolved at a concentration of 200 mg/ml in an ointment was applied in small amounts directly to three small plantar warts on the right foot of a 37 year old female. The warts were 2-5 mm in diameter. The patient was instructed to apply the cream 2-3 times per day to the three plantar warts, Patient used the medication regularly for approximately 4 weeks.

After about 8-10 days the plantar warts had noticeably decreased in size. And after one month it had completely disappeared. The patient was reassessed after 3 months there was no evidence any recurrence of the plantar warts.

EXAMPLE 4

A 0.2 ml mixture of verapamil HCl dissolved at a concentration of 2 mg/ml in an aqueous solution was injected directly under a 3 mm long skin tag in the left axillia of a 52 year old male as a subcutaneous injection. This was done daily for 5 days, and the repeated weekly for another 2 weeks.

The skin tag had disappeared by the $3^{rd}$ week.

EXAMPLE 5

A mixture of Diltiazem dissolved at a concentration of 100 mg/ml in an ointment was applied in small amounts directly to a single small 3 mm diameter plantar wart on sole under the 1st metatarsal-phallangeal joint on the left foot of a 53 year old male. The patient applied the cream to the gauze pad of a bandage and then taped the bandage over the sole of the foot so that the Diltiazem 100 mg/ml ointment was in contact with the wart. The bandage was replaced daily after showering and this was continued for six weeks. After about two weeks the plantar wart had dramatically shrunk in size to point that it was barely visible and difficult to palpate. At the six week appointment the plantar wart was not detected and the patient was advised to stop applying the Diltiazem 100 mg/ml ointment since it had completely disappeared. The patient was reassessed after 3 months there was no evidence of recurrence of the plantar wart.

EXAMPLE 6

A 45 year old woman had thick painful callouses over the lateral aspect of the 1st metatarsal-phallangeal joint on both feet. A mixture of Diltiazem dissolved at a concentration of 100 mg/ml in an ointment was given to the patient with instructions to apply the ointment 2-3 times per day in small amounts directly to only the callous locate on the 1st metatarsal-phallangeal joint of the left foot, and specifically not to use the ointment on the right foot.

The 45 year old patient applied the cream to callous of the left foot with the Diltiazem 100 mg/ml ointment for three weeks until he was reassessed by the physician/inventor. When seen by the physician at that time there had been a dramatic reduction in the thickness of the callous on the left foot, such that the callous had almost dissappeared, and the skin was now very soft and supple and was significantly improved to the point that it was difficult to detect the callous on the left foot, while the callous on the right foot which had been used as a control was unchanged.

The patient was then instructed to stop the Diltiazem ointment and was given verapamil 200 mg/ml ointment to apply 2-3 times per day to the callous of the right and left foot. After two months the callouses on both feet had shrunk in size to point that they were not visible and it was difficult to palpate any difference in the texture of the skin at the site of the callouses from the surrounding skin. The patient was reassessed after 6 months of intermittent us of the ointment and there was no evidence of recurrence of callouses.

EXAMPLE 7

A 72 year old woman had thick painful corn on the proximal interphalangeal joint of the second toe of her right foot that was causing a lot of pain when walking and wearing shoes. A mixture of Diltiazem dissolved at a concentration of 100 mg/ml in an ointment was given to the patient with instructions to apply the ointment 2-3 times per day in small amounts directly to only the corn.

The patient applied the cream to corn of the right foot with the Diltiazem 100 mg/ml ointment for on month until he was reassessed by the physician/inventor. When seen by the physician at that time there had been a noticeable reduction in the thickness of the corn on the left foot, and the patient reported a significant reduction in pain associated with wearing shoes.

The patient continued to use the Diltiazem 100 mg/ml ointment of and on for 6 months. When the patient was reassessed after 6 months the corn had dissappeared, and the skin was now very soft and supple and was significantly improved to the point that it was difficult to detect any callous or corn on the proximal interphallangeal joint of the second toe of her right foot.

EXAMPLE 8

An 58 year old male had thick painful corn on the proximal interphallangeal joint of the 5th toe of his right foot that was causing pain when walking and wearing shoes. A mixture of verapamil dissolved at a concentration of 200 mg/ml in an ointment was given to the patient with instructions to apply the ointment 2-3 times per day in small amounts directly to only the corn.

The patient applied the ointment which contained verapamil dissolved at a concentration of 200 mg/ml to corn of the right foot for on month until he was reassessed by the physician/inventor. When seen by the physician at that time there had been a noticeable reduction in the thickness of the corn on the right foot, and the patient reported a significant reduction in pain associated with wearing shoes.

The patient continued to use the verapamil ointment of and on for 6 months. When the patient was reassessed after 6 months the corn had dissappeared, and the skin was now very soft and supple and was significantly improved to the point that it was difficult to detect any callous or corn on the proximal right interphallangeal joint of the 5th toe.

EXAMPLE 9

An 58 year old male had multiple skin tags around his neck where he wore a gold necklace. A mixture of Diltiazem dissolved at a concentration of 100 mg/ml in an ointment was given to the patient with instructions to apply the ointment 1-2 times per day in small amounts directly to the skin tags.

The patient applied the ointment which contained Diltiazem dissolved at a concentration of 100 mg/ml to the skin tags for one month until he was reassessed by the physician/inventor at which time there was only a few small skin tags remaining.

The patient continued to use the Diltiazem 100 mg/ml ointment of and on for 3 months. When the patient was reassessed after 3 months the skin tags had been completely cleared.

EXAMPLE 10

A mixture of verapamil dissolved at a concentration of 200 mg/ml in an ointment was applied twice daily in small amounts directly to a hypertrophic post-operative scare on a patient that had a penile ligament release five years earlier.

Within one month the hypertrophic scar had softened and flattened noticeably, and by 5 months it was flattened to the same level as the surrounding skin and when palpated felt similar to healthy surrounding skin, but was still darker than the surrounding skin. After 2 years of follow-up, the skin was clear and normal.

EXAMPLE 11

A 51 year old male with psoriasis applied a mixture of verapamil dissolved at a concentration of 200 mg/ml in an ointment was applied twice daily in small amounts directly to a psoriatic plaques on his right leg.

Within one week the patient reported a dramatic reduction in the thickness of the plaques on the treated leg with no improvement on the left leg. When seen after two weeks of starting the application of verapamil ointment the psoriatic plaques on the treated leg had started to shrink, the plaques had significantly reduced in size and thickness, and some smaller plaques had cleared completely. After one month there had been significant clearing of the plaques on the right leg.

Subsequently the patient has tried the Diltiazem 100 mg/ml ointment on the left leg with significant clearing.

The Trifluoperazine Topical ointment 30 mg/ml was used on the right hand for one month with similar clearing. And finally Felodipine Topical ointment 100 mg/ml was used on the left hand and wrist again with significant clearing.

Due to the large size and extensive area of affected skin the patient was warned not to exceed 1.0 ml per day of the Trifluoperazine 30 mg/ml Gel topically. For the Felodipine Topical ointment 100 mg/ml, Diltiazem 100 mg/ml ointment and verapamil 200 mg/ml ointment the patient was instructed to not exceed 3 mls per day.

EXAMPLE 12

A 43 year old female with genital warts applied 0.25 ml of a mixture of verapamil dissolved at a concentration of 200 mg/ml in an ointment was applied twice daily intravaginally with a syringe.

Following at two weeks showed significant clearing of genital warts on external visualization.

An internal speculum exam at 36 days demonstrated a complete clearance of the genital warts.

EXAMPLE 13

A 17 year old female applied 0.1 ml of Trifluoperazine Topical Gel 30 mg/ml twice daily topically to a approximately 0.7 mm plantar wart that was large enough to make walking painful. A following up appointment at three weeks showed significant clearing of the patient's plantar wart. There was no irritation or erythema around the lesion and she was now actively walking and weight bearing without pain.

When seen at the six weeks follow up visit the patient reported that she had stopped using the Trifluoperazine Topical Gel for the past two weeks since she was having no pain or symptoms and the wart was no longer visible.

The Trifluoperazine Topical Gel had not been used for over 3 months when the patient was seen at 4 months and there had been no recurrence of the wart.

EXAMPLE 14

A 50 year old recreational female tennis player had bilateral thickened calluses over the right and left $5^{th}$ distal metatarsal head of both feet. These callouses were causing her significant pain and disability when she played tennis. The patient was treated with Trifluoperazine and Felodipine impregnated bandages.

Initially a water-proof bandage on which the mixture of Trifluoperazine 30 mg/ml Gel was applied to the adsorbent pad of the bandage with the pad being sized to cover the thickest area of the callous over the was right $5^{th}$ distal metatarsal head. The pad of the waterproof bandage was applied to the callous and patient was instructed to replace the bandage 1-2 times per day with a new Trifluoperazine impregnated bandage after each shower/bath.

Within one week of starting the Trifluoperazine treatment the patient reported a softening and a reduction in the thickness of the callous and reduced pain while playing tennis. When seen after two weeks of starting the application of Trifluoperazine impregnated bandages the callous on the right side had thinned and she was no longer having any pain or disability on that side, but continued to experience pain on the left side.

The patient was then given a one month supply of waterproof bandages on which the mixture of Felodipine 100 mg/ml ointment had been applied to the adsorbent pad of the bandage with the pad being sized to cover the thickest area of the callous over the was on the left $5^{th}$ distal metatarsal head. The pad of the waterproof bandage was applied to the callous and patient was instructed to replaced the bandage 1-2 times per day with a new Felodipine impregnated bandage after each shower/bath.

Subsequently the patient reported when seen in follow up after 3 weeks of using the Felodipine impregnated bandage on the left foot that she was now pain free on both sides when running and playing tennis.

EXAMPLE 15

A 32 year old male had cutaneous wart located on dorsal aspect of the metacarpal-phalangeal joint of the right index finger and was supplied with bandages on which the adsorbent pad been impregnated with verapamil dissolved at a concentration of 200 mg/ml. The patient was treated with verapamil impregnated bandages with the instructions that the pad of the waterproof bandage was applied to the wart and patient was instructed to replace the bandage 1-2 times per day with a new verapamil impregnated bandage after each shower/bath.

When seen in follow up at three weeks there was only some minor irregularity to the skin at the sit of the wart and by 4 weeks there was no evidence of the wart and the skin had healed.

EXAMPLE 16

A 19 year old female had keloid located over her located on her right hip that had formed after a dermatologist had surgically excised a mole 3 years earlier. The keloid was 19 mm×46 mm and was red raised by 7-12 mm and was very rigid and inflexible relative to the surrounding skin.

The patient was supplied with bandages on which the adsorbent pad was 2×5 cm which had been impregnated with verapamil dissolved at a concentration of 200 mg/ml. The patient was treated with verapamil impregnated bandages with the instructions that the pad of the waterproof bandage was applied to the scarred lesion and patient was instructed to replace the bandage a minimum of 1-4 times per day with a new verapamil impregnated bandage after each shower/bath.

When the patient was seen in follow up at two weeks there was noticeable flattening and softening of the scar/keloid. When to the skin at the sit of the keloid was seen at 4 weeks the keloid had flattened, was now only elevated 0-3 mm and the redness had improved. Follow up at 8 weeks showed that the patient was now very pleased with the cosmetic improvement, and was no longer using the verapamil bandages. At that time the patient was given several 3 ml syringes with verapamil 200 mg/ml ointment and told to apply it twice daily on a long term prn basis. Follow up at 6 months showed continued maintenance and no relapse of the initial cosmetic improvement.

EXAMPLE 17

A 48 year old African American male had keloids that had formed over several areas of the donor site scar from a previous hair transplant several years ago over the occipital area of the scalp from mastoid process to mastoid process. The keloids over the mastoid process on right side were initially treated with Felodipine 100 mg/ml ointment. The patient had been given instructions to apply the Felodipine 100 mg/ml ointment several times per day to the right side only and the patient was seen weekly in follow up.

After 1 week their was noticeable softening of the keloid over the right mastoid process. After 2 weeks their was noticeable flattening and continued softening of the keloid over the right mastoid process. By six weeks the keloid had flattened to the level of the adjoining skin and FUE grafts harvested from another site and were transplanted into the keloid which was devoid of hairs to affect hair coverage.

Then patient was supplied with a several 5 ml syringes with removable caps that contained a mixture of Diltiazem dissolved at a concentration of 100 mg/ml in an ointment and he was told to apply this to the keloid over the left mastoid area. After 1 week their was noticeable softening of the keloid over the left mastoid process. After 2 weeks their was noticeable flattening and continued softening of the keloid over the left mastoid process. By six weeks the keloid had flattened to the level of the adjoining skin and FUE grafts harvested from another site and were transplanted into the keloid which was devoid of hairs to affect hair coverage.

Follow up at 6 and 9 months showed continued maintenance and no relapse of the initial cosmetic improvement and normal growth of the hair follicles transplanted into the keloids. As well their was no new keloid formation from the now FUE graft donor sites where the patient had been instructed to apply Diltiazem and Feldopine for two weeks twice daily to the donor surgical sites.

EXAMPLE 18

A 36 year old male applied 0.1 ml of Trifluoperazine Topical Gel 30 mg/ml twice daily topically to several genital warts and a skin tag in the right axillary area.

When seen in a following up appointment at three weeks showed significant clearing of the patient's genital wart and the skin tag. The patient was advised to continue for one more week and the to stop applying the Trifluoperazine Topical ointment. Follow up a month later showed complete clearing of the skin tag and of the genital warts.

EXAMPLE 19

A 28 year old male applied 0.1 ml of Diltiazem supplied in 3 ml syringes with removable caps dissolved at a concentration of 100 mg/ml in an ointment twice daily topically to several genital warts.

When seen in a following up appointment at three weeks showed significant clearing of the patient's genital wart and the skin tag. The patient was advised to continue for one more week and the to stop applying the Diltiazem dissolved at a concentration of 100 mg/ml in an ointment. Follow up at 5 weeks showed complete clearing of the genital warts.

Although this disclosure has described and illustrated certain preferred embodiments of the invention, it is to be understood that the invention is not restricted to those particular embodiments.

The invention claimed is:

1. A method of removing an hyperplastic skin lesion
of the dermis and epidermis of a mammal, wherein said hyperplastic skin lesion is selected from the group consisting of calluses, corns, plantar warts, genital warts, cutaneous warts, and skin tags, comprising:
administering to said lesion or locus thereof a therapeutically effective amount of a composition comprising a blocker selected from the group consisting of a calcium channel blocker, a calmodulin blocker and a pharmaceutically acceptable diluent or carrier.

2. A method according to claim 1, wherein said calcium channel blocker is verapamil.

3. A method according to claim 1, wherein said calcium channel blocker is diltiazem.

4. A method according to claim 1, wherein said calcium channel blocker is felodipine.

5. A method according to claim 1, wherein said calmodulin blocker is trifluoperazine.

6. A method according to claim 1, wherein said composition is in the form of a cream, spray, gel, ointment or patch.

* * * * *